(12) United States Patent
Marcussen

(10) Patent No.: US 6,384,293 B1
(45) Date of Patent: May 7, 2002

(54) DRESSING

(75) Inventor: Jan Marcussen, Taastrup (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/509,521

(22) PCT Filed: Sep. 25, 1998

(86) PCT No.: PCT/DK98/00419

§ 371 Date: Mar. 30, 2000

§ 102(e) Date: Mar. 30, 2000

(87) PCT Pub. No.: WO99/16396

PCT Pub. Date: Apr. 8, 1999

(30) Foreign Application Priority Data

Sep. 30, 1997 (DK) ............................................. 1125/97

(51) Int. Cl.⁷ ................................................ A61F 13/00
(52) U.S. Cl. ............................. 602/41; 602/42; 602/43; 602/52
(58) Field of Search .............................. 602/41–47, 52, 602/55, 57–58; 206/440–441, 444; 604/307; 424/445

(56) References Cited

U.S. PATENT DOCUMENTS 3,563,237 A * 2/1971 Maxwell ..................... 206/59
RE31,886 E * 5/1985 Hodgson ..................... 128/156
5,266,371 A * 11/1993 Sugii et al. ..................... 602/57
5,584,801 A * 12/1996 Kuroyanagi et al. ......... 424/447
5,713,842 A * 2/1998 Kay ............................ 206/444

* cited by examiner

Primary Examiner—Denise M. Pothier
Assistant Examiner—Lalita M. Hamilton
(74) Attorney, Agent, or Firm—Jacobson Holman, PLLC

(57) ABSTRACT

A dressing for covering a portion of the anatomical surface of a living being, the dressing being able to adhere to the skin, the mucosa and/or a wound on a protruding portion of a living being without exposing the skin to a significant stress after application and the dressing comprising a substantially water-impervious film and a skin-friendly adhesive, which dressing has a low modulus allowing an easy deformation during application but yet a sufficiently high elasticity to essentially prevent deformation of wrinkles after application, wherein the dressing is optionally covered in part or fully by one or more release liners or cover films to be removed before or during application and wherein the dressing has the general form of a boomerang which facilitates the perfect adaptation during application to cover cracks at the tip of, e.g., a finger or toe at the edge of the nail.

16 Claims, 1 Drawing Sheet

DRESSING

BACKGROUND OF THE INVENTION

1. Field of the Invention

The present invention relates to dressings, in particular dressings for covering a portion of the anatomical surface of a living being, the use of a film being able to adhere to the skin for forming such dressings and a method of treating a portion of the anatomical surface of a living being, especially a protruding part of the body.

2. Description of the Related Art

Conventionally, dressings for the treatment or prevention of wounds or pressure sores or even unbroken skin are essentially flat dressings which are sufficiently moldable to be applied to flat or slightly curved areas of the body. Such flat dressings are not very suitable for applying on protruding parts of the body or joints such as elbows, heels or especially the tips of fingers or toes or parts of the body having a very pronounced curvature such as the inter digital area as they often wrinkle and focus stresses in the dressing often causing slipping of the adhesive and unintended detachment of the dressing.

Published European patent application No. EP 0 676 183 A1 discloses conformable adhesive bandages which are stated to be extremely conformable, and yet resilient enough to maintain their shape after being subjected to forces caused by movement of the wearer. The bandages contain at least three elements: the backing material, which protects the wound-covering portion of the bandages; the wound covering portion of the products which contacts the wound and provides a reservoir for the wound exudate; and the adhesive composition, which holds the product in place around the wound. Furthermore, it is stated that the recovered energy of the bandage disclosed in EP 0 676 183 A1 should be relatively high, so as to assure that the bandage will not permanently deform in use. Such recovered energy built into a dressing or bandage will inevitably try to retract it to its original shape if stretched during use and expose the skin to a significant stress which will cause nuisance to the user.

U.S. Pat. No. 4,346,700 discloses pressure sensitive adhesive sheet materials such as tapes and surgical drapes, which are stated to be conformable and have viscoelastic properties similar to human skin. Furthermore, it is stated that the materials exhibit stress relaxaton with time, having relaxation properties to recover to near original unstressed length when all stress is removed.

Published European patent application No. EP 0 457 977 A1 discloses a wound dressing comprising a pad of soft polyurethane foam, one surface layer of which is hydrophilic and a backing layer of which is hydrophobic and a sheet or strip of a soft conformable polyether foam having an adhesive on one surface thereof, the dressing showing a sufficient elasticity to readily conform for extended periods of time to difficult areas such as elbow joints and knee joints.

U.S. Pat. No. 4,741,949 discloses an elastic polyetherester non-woven web formed by melt blowing fibres composed of a polyester.

A liquid plaster in the form of a solution of a polymer in ethyl acetate is known under the trade mark Nobecutan®. Such a plaster will naturally conform to the area onto which it is applied but is highly unsuitable for application on broken or irritated skin due to the content of ethyl acetate giving a severe local irritation.

Until now no reference discloses dressings being able to adhere to the skin, the dressings being flexible and moldable so as to adapt to the contour of the part of the body to be covered and the dressings adhering to the skin and being able to adapt to and follow the movements of tips or roots of fingers or toes without exposing the skin to a significant stress after application and being applicable directly on broken or irritated skin without unpleasant feeling.

One object of the invention is to provide a dressing being moldable and flexible so as to be able to adapt to the contour of the part of the body to be covered and the dressing adhering to the skin and being able to adapt to and follow the movements of the skin of especially tips or roots of fingers or toes. Another object of the invention is to provide a dressing which may prevent, e.g., wearing or abrasion damages, the dressing being provided with a surface which may be adapted to the environment in which the dressing is to be used giving a longer effective time of use for the dressing between the change of the dressing.

A still further object of the invention is to provide processes for the preparation of such dressings.

The dressing of the present invention fulfills the above objects to a degree not seen hitherto.

BRIEF SUMMARY OF THE INVENTION

The invention relates to a dressing for covering a portion of the anatomical surface of a living being, the dressing being able to adhere to the skin, the mucosa and/or a wound on any portion of a living being, and the dressing being moldable so as to adapt to the contour of the part of the body to be covered.

Furthermore, the invention relates to the use of a film being able to adhere to the skin, the film having a low modulus when deformed and a deformation created before or during application of the dressing for forming a dressing for covering a portion of the anatomical surface of a living being.

The invention also relates to a method of treating a portion of the anatomical surface of a living being comprising applying a dressing being able to adhere to the skin, the dressing being moldable so as to adapt to the contour of the part of the body to be covered.

BRIEF DESCRIPTION OF THE DRAWINGS

The invention is explained more in detail with reference to the drawings in which.

DETAILED DESCRIPTION OF THE INVENTION

Figure 1:
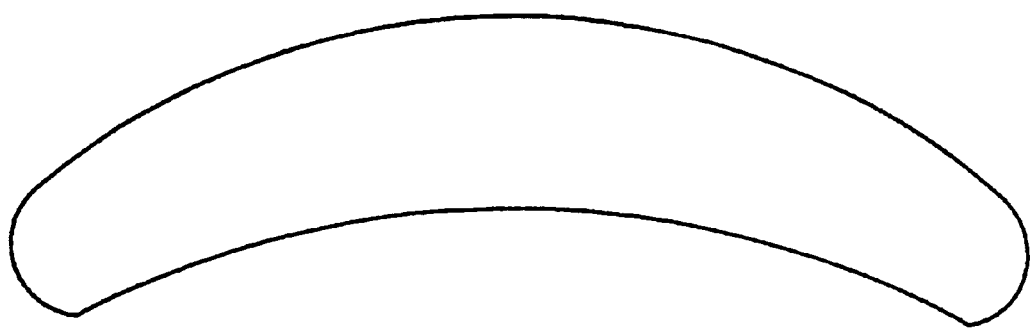
FIG. 1 shows the contour of one embodiment of a "boomerang shaped" wound dressing according to the invention.

The present invention relates to a dressing for covering a portion of the anatomical surface of a living being, the dressing being able to adhere to the skin, the mucosa and/or a wound on a protruding portion of a living being without exposing the skin to a significant stress after application and the dressing comprising a substantially water-impervious layer or film and a skin-friendly adhesive, which dressing has a low modulus allowing an easy deformation during application but yet a sufficiently high elasticity to essentially prevent formation of wrinkles after application, wherein the dressing is optionally covered in part or fully by one or more release liners or cover films to be removed before or during application and wherein the dressing has the general form of a boomerang.

The dressing of the invention has surprisingly rendered it possible, when applying a dressing to a protruding part of the body to stretch the dressing to suit the size of the part of the body to be covered whereafter the dressing will adapt rather tightly to the contour of the part of the body to be covered and adhere to it without exposing the skin to a significant stress after application. The dressing will adhere to the skin and follow later movements like a "second skin" which will ensure that the dressing does not tauten the skin or constrict parts of the body. Thus, the dressing of the invention shows a low modulus against deformation and retains a sufficient elasticity to follow the movements of the skin without formation of wrinkles. The reduced stress will give a long wear time and the dressing of the invention only needs to be changed when it is "technically necessary" and many changes due to slipping are avoided. The general form of a boomerang facilitates the perfect adaptation during application to cover skin abnormalities such as cracks at the tip of, e.g., a finger at the edge of the nail or in area around the root of a finger or a toe.

The dressing preferably has rounded ends and preferably has smooth edges without scratches or being frayed at the edge. This is especially preferred at the "end" portions thereof avoiding points of attack for initiating an unintended rolling-up of the dressing.

The modulus against deformation and elasticity of a dressing of the invention is a result of the combined properties of the substantially water-impervious layer or film and the skin friendly adhesive. Thus, in one extreme, the substantially water-impervious layer or film is elastic and the skin friendly adhesive is plastic, and in the opposite extreme, the substantially water-impervious layer or film is plastic and the skin friendly adhesive is elastic. Any combination of properties there between fulfilling the requirements will be suitable according to the invention.

The skin-friendly adhesive may be any skin-friendly adhesive known per se, e.g., an adhesive comprising hydrocolloids or other moisture absorbing constituents for prolonging the time of use. The adhesive may suitably be of the type disclosed in GB patent specification No. 1 280 631, in DK patent specifications Nos. 127,578, 148,408, 154,806, 147,226 and 154,747, in EP published application Nos. 0 097 846 and 0 415 183, in SE published application No. 365,410, in WO publication No. 88/06894, in U.S. Pat. No. 4,867,748, and in NO published applicaton No. 157,686. Especially preferred are the adhesives disclosed in U.S. Pat. Nos. 4,367,732 and 5,051,259 and DK patent specification No. 169,711.

The water impervious layer or film may be of any suitable material known per se for use in the preparation of wound dressings, e.g., a foam, a non-woven layer or a polyurethane, polyethylene, polyester or polyamide film. In accordance with the invention it has surprisingly been found that the use of a thinner backing layer or film than is normally used when preparing medical dressings result in an improved stretcheability and adaptability at the same time as the modulus is reduced. These properties are obtained using the same load of adhesive as is conventionally used, and thus, the conventional properties of the adhesive are retained as opposed to the case in which the load of adhesive was lowered giving a risk of insufficient tack and adhesive properties.

Using a layer or film having a low modulus allowing an easy deformation during application but yet a sufficiently high elasticity to essentially prevent deformation after application renders the dressing apt for application on, e.g., tips or roots of fingers or toes of various sizes as the dressing easily adapts to the actual curvature and still has a sufficient elasticity to ensure that the dressing does not form wrinkles and that it does not act ligating.

A dressing of the invention is thus especially apt for use on cracks on the tip of a finger or of a toe as it allows for a stretching of the dressing to be sufficiently deformed to be able to cover a protruding part of the body, e.g., a finger, whereafter the dressing quickly adapts to the protruding part of the body and adheres to the same. The dressing of the invention may be wrapped around an extremity such as a finger or stretched to cover, e.g., the tip of a finger or a toe around the edge of the nail. The dressing of the invention is thus very suitable for covering the area between fingers or toes and is also suitable for applying around the root of a finger or toe or in connection with joints such as elbows, knees or ankles where skin abnormalities such as cracks often occur.

The water impervious layer or film is preferably a low-friction flexible polymer film reducing the risk of unwanted stress in the area of the crack impeding the healing of a crack on a very exposed site.

A suitable material for use as a water impervious film is a polyurethane. A preferred low friction film material is disclosed in U.S. Pat. No. 5,643,187. A preferred thickness of this film is below 20 microns, more preferred about 12–18 microns, thus resulting in a significant decrease of the modulus, compared to a film that is normally used when preparing medical dressings. An improved stretcheability and adaptability is obtained at the same time as the modulus is reduced.

The force used for stretching a dressing according to the invention 100% is below 4.5 N, preferred below 2.5 N, more preferred about 0.6 to 1.8 N.

The dressing of the invention preferably has a ratio between the length and the width of from about 1.1:1 to about 12:1, more preferred from about 1.5.1 to 10:1 and most preferred from about 1.5:1 to 6:1.

In order to ensure a suitable modulus in a longitudinal direction, it is preferred that the width of the dressing does not exceed 20 mm, preferably not exceeding 12 mm.

The dressing of the invention preferably has bevelled edges in order to reduce the risk of "rolling-up" the edge of the dressing thus reducing the wear-time and thus disturbing and prolonging the healing of cracks normally healing slowly on tips of fingers or toes due to physical stress. A bevelling may be carried out discontinuously or continuously in a manner known per se, e.g., as disclosed in EP patent No. 0 264 299 or in U.S. Pat. No. 5,133,821.

A protective cover or release liner may for instance be siliconized paper. It does not need to have the same contour as the dressing, e.g., a number of dressings may be attached to a larger sheet of protective cover. The protective cover is not present during the use of the dressing of the invention and is therefore not an essential part of the invention.

Furthermore, the dressing of the invention may comprise a "non touch" grip known per se for applying the dressing to the skin without touching the adhesive layer. Such a non-touch grip is not present after application of the dressing.

It is advantageous to provide a dressing of the invention with components for treatment or prophylaxis of formation of wounds and/or skin abnormalities, e.g., with emollients or an active constituent, e.g., retinoids for treating or preventing formation of psoriasis, eczema, callous skin, corns, insect bites, acne or blisters. The dressing of the invention may also contain medicaments such as bacteriostatic or bactericide compounds, e.g., iodine, Iodopovidone complexes, chioramine, chlorohexidine, silver salts, zinc or salts thereof, tissue-healing enhancing agents, e.g., RGD tripeptides and the like, enzymes for cleansing of wounds, e.g., pepsin, trypsin and the like, pain relieving agents, or agents having a cooling effect which is also considered an aspect of the invention.

A dressing according to the invention may be prepared by a manner known per se for the preparation of medical dressings by substituting the raw materials and it will be routine for the skilled in the art to adapt the process parameters to the actual materials.

The invention also relates to the use of a film having a low modulus being able to adhere to the skin for preparing a dressing for covering a portion of the anatonical surface of a living being, the dressing being able to adhere to the skin, the mucosa and/or a wound on a protruding portion of a living being without exposing the skin to a significant stress after application and the dressing comprising a substantially water-impervious layer or film and a skin-friendly adhesive, which dressing has a low modulus allowing an easy deformation during application but yet a sufficiently high elasticity to essentially prevent formation of wrinkles after application and wherein the dressing is optionally covered in part or fully by one or more release liners or cover films to be removed before or during application.

Further, the invention relates to a method of treating a portion of the anatomical surface of a living being, especially a protruding part of the body by applying a dressing for covering the portion of the anatomical surface of a living being, the dressing being able to adhere to the skin, the mucosa and/or a wound on a protruding portion of a living being without exposing the skin to a significant stress after application and the dressing comprising a substantially water-impervious layer or film and a skin-friendly adhesive, which dressing has a low modulus allowing an easy deformation during application but yet a sufficiently high elasticity to essentially prevent formation of wrinkles after application and wherein the dressing is optionally covered in part or fully by one or more release liners or cover films to be removed before or during application. The conditions to be treated may be abnormalities like dry skin, cracks or the like.

The invention is explained more in detail with reference to the drawings showing preferred embodiments of the invention in the form of a "boomerang shaped" wound dressing especially suitable for finger cracks on the tip of a finger or toe.

The long and narrow embodiment shown in FIG. 1 is especially suitable for use on fingers as this embodiment is especially suitable for winding around the tip of a finger. When applying the dressing, the protective layer is removed and the dressing is applied on the crack on the tip of the finger or toe, and the two ends of the dressing are stretched so that they follow the contour of the fingernail. When the dressing is applied, the "boomerang shape" has shown to be very efficient for a smooth adaptation to the contour, of e.g., the limit of a finger nail.

Figure 2:
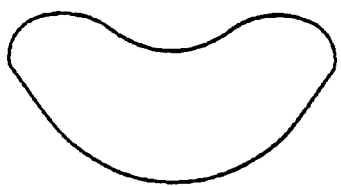
FIG. 2 shows the contour of another embodiment of a "boomerang shaped" wound dressing according to the invention being relatively shorter and wider.
Figure 3:
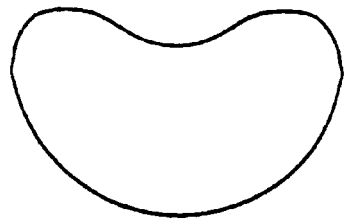
FIG. 3 shows the contour of a further embodiment of a "boomerang shaped" wound dressing according to the invention being even more compact.

The relatively more short and wider embodiments of "boomerang shaped" wound dressings according to the invention shown in FIG. 2 and 3 are suitable for use on thick fingers such as thumbs or especially for toes.

What is claimed is:

1. A dressing for covering a portion of the anatomical surface of a living being, the dressing being able to adhere to at least one of skin, mucosa and a wound on a protruding portion of the living being without exposing the skin to a significant stress after application, the dressing comprising a substantially water-impervious layer or film and an adhesive, which dressing has a low modulus allowing an easy deformation during application and a sufficiently high elasticity to essentially prevent formation of wrinkles after application, a force necessary to stretch the dressing 100% being below 4.5 N, the dressing further having arcuate longitudinal sides which are generally parallel to one another in a center portion of said dressing and which taper toward one another at each end of said dressing, each end having rounded corners to reduce rolling up of the dressing.

2. The dressing as claimed in claim 1, wherein the dressing is intended for use on a protruding portion of the body.

3. The dressing as claimed in claim 2, wherein the substantially water-impervious film is of polyurethane.

4. The dressing as claimed in any of claims 1–3, wherein the dressing has a ratio between the length and the width from about 1.1:1 to about 12:1.

5. The dressing as claimed in claim 1 wherein the dressing has a ratio between its length and its width of from about 1.1:1 to about 12:1.

6. The dressing as claimed in claim 1, wherein said tapered end portions have rounded corners.

7. The dressing as claimed in claim 1, wherein said substantially water-impervious layer or film has a thickness of less than 20 microns.

8. The dressing as claimed in claim 7, wherein said substantially water-impervious layer or film has a thickness of between 12–18 microns.

9. The dressing as claimed in claim 1, wherein the force necessary to stretch the dressing 100% is below 2.5 N.

10. The dressing as claimed in claim 1, wherein the force necessary to stretch the dressing 100% is between 0.6 and 1.8 N.

11. A dressing for covering a portion of the anatomical surface of a living being, and being able to adhere to at least one of skin, mucosa and a wound on a protruding portion of the living being without exposing the skin to a significant stress after application, the dressing comprising a substantially water-impervious layer or film having a thickness of less than 20 microns and an adhesive, said dressing having a low modulus allowing easy deformation during application and a sufficiently high elasticity to essentially prevent formation of wrinkles after application, said dressing further having arcuate longitudinal sides which are generally parallel to one another in a center portion of said dressing and which taper toward one another at each end of said dressing.

12. The dressing as claimed in claim 11, wherein each end has rounded corners and a beveled edge to reduce rolling up of the dressing.

13. The dressing as claimed in claim 11, wherein said substantially water-impervious layer or film has a thickness of between 12–18 microns.

14. The dressing as claimed in claim 11, wherein a force necessary to stretch the dressing 100% is below 4.5 N.

15. The dressing as claimed in claim 14, wherein a force necessary to stretch the dressing 100% is below 2.5 N.

16. The dressing as claimed in claim 15, wherein the force necessary to stretch the dressing 100% is between 0.6 and 1.8 N.

* * * * *